United States Patent
Duncan

(10) Patent No.: US 11,083,596 B2
(45) Date of Patent: Aug. 10, 2021

(54) MINIMALLY INVASIVE TRANSFORAMINAL LUMBAR INTERBODY FUSION

(71) Applicant: Jan William Duncan, Los Angeles, CA (US)

(72) Inventor: Jan William Duncan, Los Angeles, CA (US)

(*) Notice: Subject to any disclaimer, the term of this patent is extended or adjusted under 35 U.S.C. 154(b) by 60 days.

(21) Appl. No.: 16/586,256

(22) Filed: Sep. 27, 2019

(65) Prior Publication Data

US 2020/0100907 A1    Apr. 2, 2020

Related U.S. Application Data

(60) Provisional application No. 62/739,205, filed on Sep. 29, 2018.

(51) Int. Cl.
*A61F 2/46*     (2006.01)
*A61B 17/16*    (2006.01)
*A61B 17/17*    (2006.01)

(52) U.S. Cl.
CPC ............ *A61F 2/46* (2013.01); *A61B 17/1633* (2013.01); *A61B 17/1671* (2013.01); *A61B 17/1725* (2013.01); *A61B 17/1757* (2013.01); *A61F 2002/4635* (2013.01)

(58) Field of Classification Search
CPC ... A61F 2/46; A61B 17/1633; A61B 17/1757; A61B 17/1671
See application file for complete search history.

(56) References Cited

U.S. PATENT DOCUMENTS

| | | | | |
|---|---|---|---|---|
| 3,128,768 A | * | 4/1964 | Geistauts | A61B 17/1633 606/180 |
| 6,287,313 B1 | * | 9/2001 | Sasso | A61B 17/1671 |
| 6,669,698 B1 | * | 12/2003 | Tromanhauser | A61B 17/1615 606/104 |
| 2005/0261692 A1 | * | 11/2005 | Carrison | A61B 17/1633 606/79 |
| 2006/0041268 A1 | * | 2/2006 | Shores | A61C 1/10 606/180 |
| 2012/0130375 A1 | * | 5/2012 | Gillard | A61B 17/1617 606/80 |
| 2012/0130381 A1 | * | 5/2012 | Germain | A61B 17/3472 606/84 |
| 2014/0277140 A1 | * | 9/2014 | Jarolem | A61B 17/86 606/247 |
| 2020/0038070 A1 | * | 2/2020 | Suddaby | A61F 2/4405 |

* cited by examiner

*Primary Examiner* — Christian A Sevilla

(74) *Attorney, Agent, or Firm* — Gavrilovich, Dodd & Lindsey LLP

(57) ABSTRACT

This disclosure presents a MITLIF procedure. The procedure uses a single incision on one side and pedicle screws are placed on that side and through the same incision a facet screw is placed on the opposite side using a series of jigs, and, for example, the hole cutter, drill, guide shaft and screw driver described herein.

3 Claims, 7 Drawing Sheets

MINIMALLY INVASIVE TRANSFORAMINAL LUMBAR INTERBODY FUSION

CROSS REFERENCE TO RELATED APPLICATION

This application claims priority to U.S. Provisional Application No. 62/739,205, filed Sep. 29, 2019, the disclosure of which is incorporated herein by reference.

BACKGROUND

There are numerous research papers documenting the advantages of minimally invasive surgery. Such advantages include less blood loss, shorter operating duration, shorter hospitals stay, and less muscular damage.

Segmental spinal fusions which stabilize two or more adjacent segments of the spine are performed for painful degenerative disc disease, recurrent disc herniations, spinal stenosis, spondylolysis and spondylolisthesis. Over the past several decades a wide variety of fusion techniques and instrumentation have evolved.

Efforts have been made to extend minimally invasive surgery techniques to spinal fusion and repair, including transforaminal lumbar interbody fusions (minimally invasive transforaminal lumbar interbody fusion (MITLIF)). Such techniques have demonstrated equally good long term outcomes compared to non-MITLIF procedures.

SUMMARY

The disclosure provides a method of minimally invasive transforaminal lumbar interbody fusion (MITLIF) comprising: drilling a hole in a spinous process using a hole cutter; inserting a guide shaft into the hole of the spinous process down to a facet joint; inserting a drill through the inner diameter of the drill guide; drilling a hole in the facet joint; inserting a facet screw and screwdriver though the inner diameter of the drill guide; and seating the screw into the facet joint. In one embodiment, the method further comprises placing pedicle screws on the opposite side of the spinous process. In another embodiment, an access for placement of the pedicle and facet screws is the same access for both.

The disclosure also provides a surgical system for carrying out the method of the invention. In one embodiment, the surgical system comprises a surgical guide shaft device comprising a first end, a second end, a lumen extending and open from the first end to the second end and having and internal diameter "D" and an external diameter "X", wherein the second end comprises a traction system comprising one or more prong(s) and traction feet; a drill bit comprising a shaft having one or more stabilization collars a drill tip at one end of the drill bit wherein the one or more stabilization collars having a diameter smaller than the diameter D of the guide shaft such that the collars can be moved along the length of the shaft while maintaining the shaft of the drill substantially centered in the lumen of the guide shaft; and a screw-driver comprising a shaft, a tip for engaging a screw and one or more stabilization collars, wherein the one or more stabilization collars have a diameter smaller than the diameter D of the guide shaft such that the collars can be moved along the length of the shaft while maintaining the shaft of the screw driver substantially centered in the lumen of the guide shaft.

The disclosure also provides a surgical guide shaft device for minimally invasive transforaminal lumbar interbody fusion comprising a tube having at least one wall, a first end and second end, the tube having a diameter "D", wherein the second end comprises a traction system having at least one prong and a plurality of traction feet. In one embodiment, the at least one prong comprises at least two prongs. In a further embodiment, the at least two prongs are about 2 mm long and about 0.5-1.5 mm in diameter with a tapered/pointed end extending from the at least one wall and parallel with the length dimension of the tube. In another embodiment, the guide shaft device further comprises a handle affixed to the outside of the tube suitable for grasping and manipulation by a surgeon.

The disclosure also provides a surgical drill bit comprising a shaft having a first end and second end, a drill head at the first end of the shaft, one or more stabilization collars, wherein the stabilization collars have a diameter greater than the diameter of the shaft and located between the first end and second end of the shaft. In one embodiment, wherein the one or more stabilization collars comprises one stabilization collar and wherein the length of the collar is about 10% to about 90% the length of the shaft. In another embodiment, the one or more stabilization collars comprise two stabilization collars and wherein each of the stabilization collars are about 2% to about 30% the length of the shaft and wherein the stabilization collars are separated from one another along the length of the shaft.

The disclosure also provides a surgical screw driver comprising a shaft having a first end and second end, a head at the first end of the shaft for engaging a screw, one or more stabilization collars, wherein the stabilization collars have a diameter greater than the diameter of the shaft and located between the first end and second end of the shaft. In one embodiment, the one or more stabilization collars comprises one stabilization collar and wherein the length of the collar is about 10% to about 90% the length of the shaft. In another embodiment, the one or more stabilization collars comprise two stabilization collars and wherein each of the stabilization collars are about 2% to about 30% the length of the shaft and wherein the stabilization collars are separated from one another along the length of the shaft.

DETAILED DESCRIPTION

Figure 1:
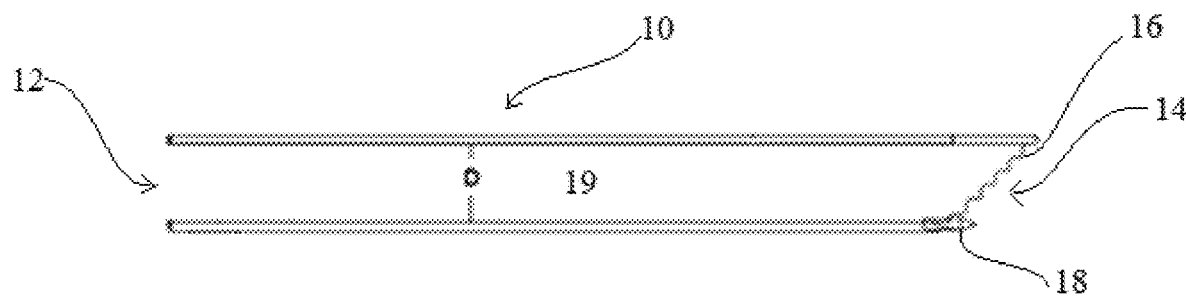
FIG. 1 provides a schematic of a guide shaft of the disclosure.

As used herein and in the appended claims, the singular forms "a," "an," and "the" include plural referents unless the context clearly dictates otherwise. Thus, for example, reference to a "a screw" includes a plurality of screws and reference to "the pedicle" includes reference to one or more pedicles and equivalents thereof known to those skilled in the art, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to any term that is presented in one or more publications that is similar to, or identical with, a term that has been expressly defined in this disclosure, the definition of the term as expressly provided in this disclosure will control in all respects.

Also, the use of "and" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The term "about" as used herein can allow for a degree of variability in a value or range, for example, within 10%, within 5%, or within 1% of a stated value or of a stated limit of a range. When a range or a list of sequential values is given, unless otherwise specified any value within the range or any value between the given sequential values is also disclosed.

One attempt to simplify the transforaminal lumbar interbody fusion (TLIF) procedure has been to use unilateral fixation. The results have been controversial. Some research papers have shown that unilateral fixation has equal outcome compared to bilateral fixation. There are other papers that showed that unilateral fixation has a higher incidence of displaced spacers than bilateral fixation. Bilateral fixation is normally performed by making an incision on both sides of the vertebrae, placing a K-wire into the pedicle, followed by placing the pedicle screw over the K-wire. A series of jigs are then used for the placement of the rod and set screws.

As early as ten years ago the biomechanical study by Slucky et al. (Spine J, 6:78-85, 2006) showed that pedicle screws on one side and the facet screws on the other side had equal strength compared to bilateral pedicle screws. They noted that it would be desirable if a method of placing this type of fixation could be done through a minimally invasive approach. A clinical series comparing bilateral pedicle screws fixation to pedicle screws on one side and the facet screws on the other side showed that the latter was equally effective on a clinical bases.

Complications of pedicle screw placement include duration of procedure, significant tissue dissection and muscle retraction, misplaced screws with neural and/or vascular injury, excessive blood loss, need for transfusions, prolonged recovery, incomplete return to work, excess rigidity leading to adjacent segmental disease requiring further fusions and re-operations. Further advances of pedicle screw fixation including minimally invasive and image-guided technology, and the development of flexible rods have imperfectly addressed some but not all of these issues. Transfacet screws and similar embodiments entail the use of short or long screws which provide static facet alignment without motion calibration.

This disclosure presents a prospective series of MITLIF procedures. What makes this procedure unique is that a single incision is used on one side and pedicle screws are placed on that side and through the same incision a facet screw is placed on the opposite side. The disclosure provides both the methodology for performing this MITLIF as well as devices useful for performing the method.

Turning to FIG. 1, the figure depicts a guide shaft 10 comprising a first end 12, a second end 14, a lumen 19 having and internal diameter "D" and an external diameter "X". The guide shaft 10 can be made of any resilient sterilizable and biocompatible material (e.g., surgical steel). Second end 14 comprises a traction system comprising prong(s) 18 and traction feet 16.

Figure 2A:
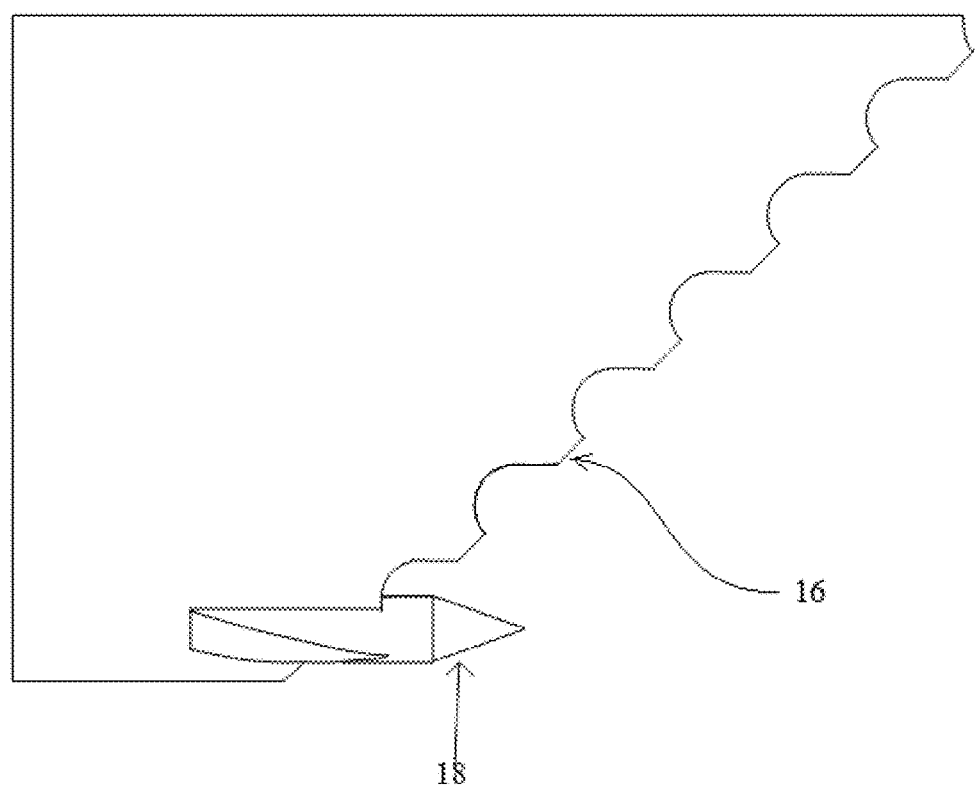
FIG. 2A-B provide schematics of the traction end of the guide shaft in further detail.
Figure 2B:
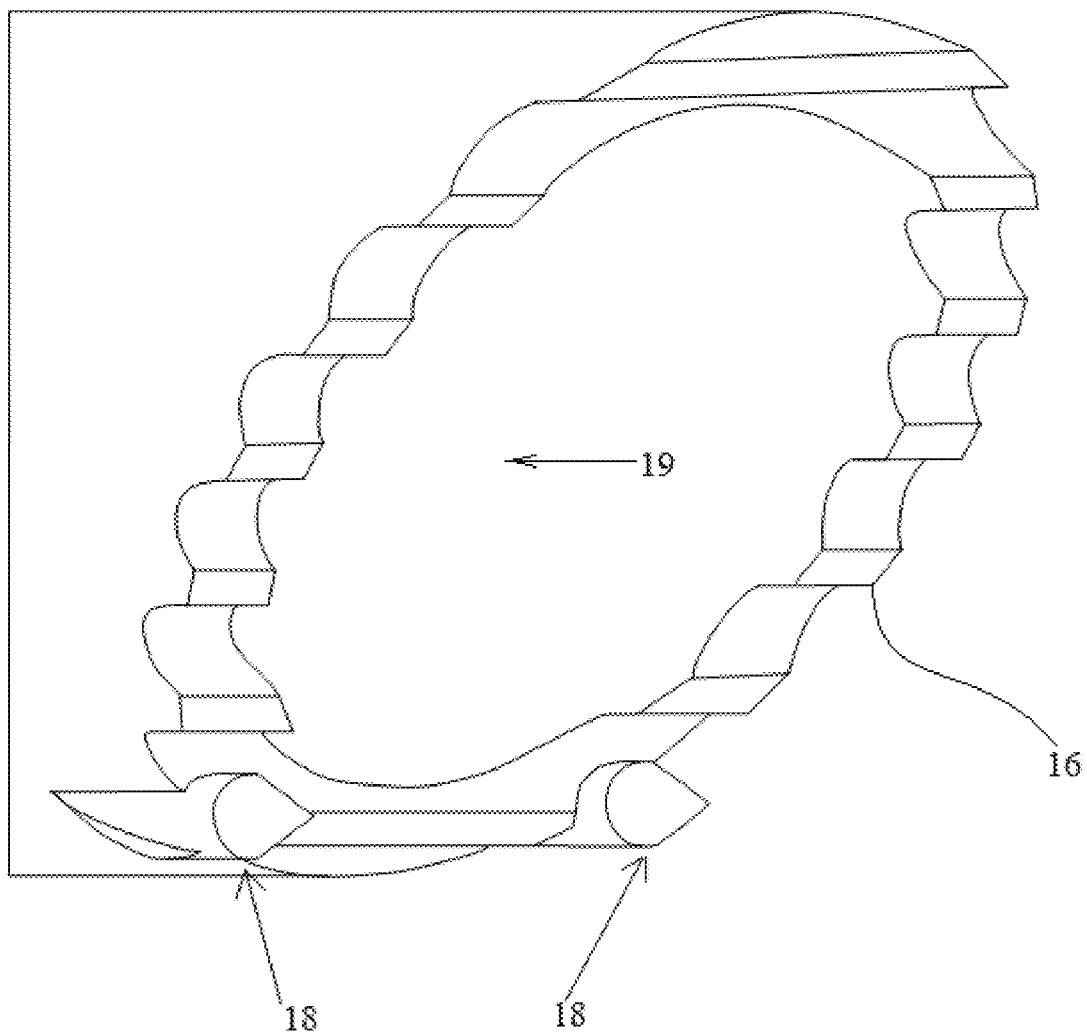

FIGS. 2A-B depict second end 14 in further detail. FIG. 2B depicts second end 14 having two prongs 18. In one embodiment, the prongs 18 are 1-3 mm long (e.g., about 2 mm long) and have a diameter of about 0.5-1.5 mm (e.g., about 1 mm).

Figure 3:
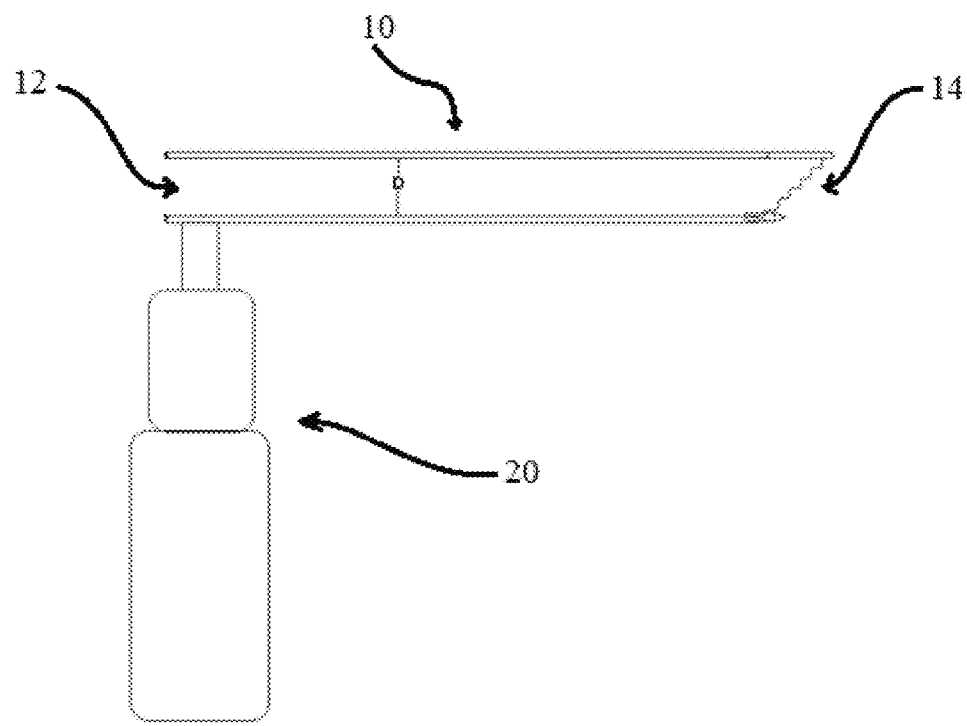
FIG. 3 provides a further schematic of a guide shaft of the disclosure including a handle for guiding the guide shaft.

FIG. 3 shows guide shaft 10 further including a handle 20 for used during the procedure to hold an manipulate the guide shaft 10 during the procedure and placement through a spinal process.

Figure 4:
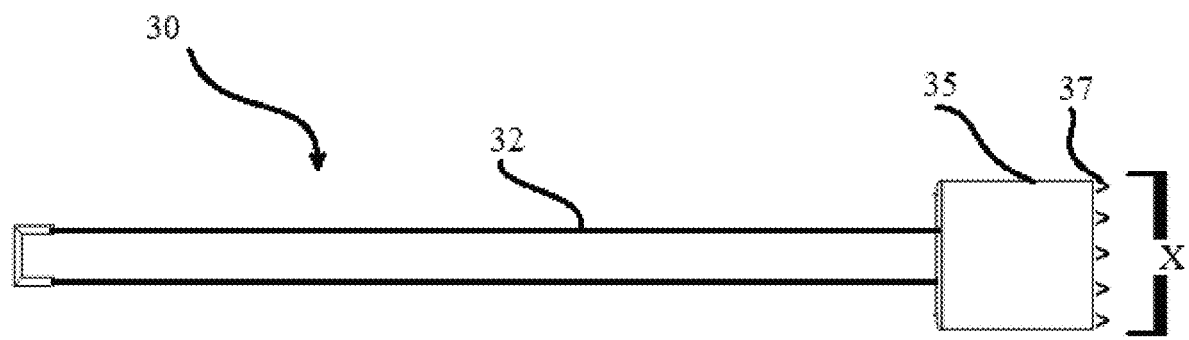
FIG. 4 provides a schematic of a hole cutter.

FIG. 4 shows a hole cutter 30. Hole cutter 30 includes a shaft 32, head 35 comprising teeth 37 used for cutting a hole in a spinal process. The head 35 has a diameter "X" that is equal to or slightly larger (e.g., micrometers to a millimeter larger) than the outside diameter of the guide shaft 10. The diameter of the head 35 should be large enough to drill a hole in a spinal process such that the guide shaft 10 can be inserted through the hole. The hole cutter typically comprise a tungsten carbide, stainless steel or other suitable surgical drill material.

Figure 5:
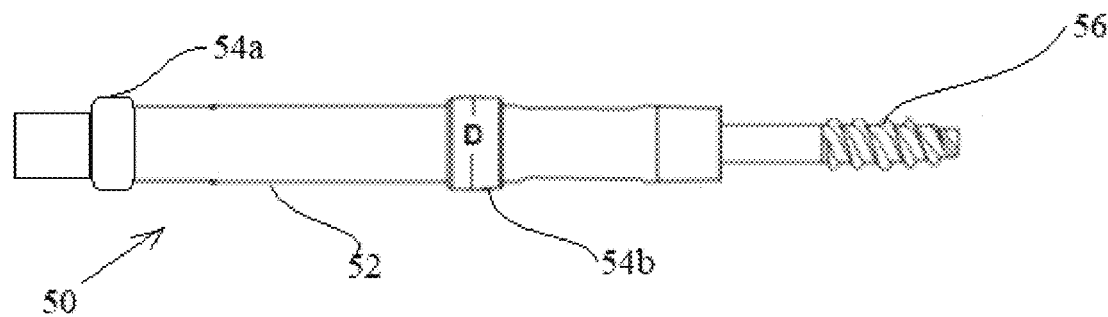
FIG. 5 provides a diagram of a drill of the disclosure.
Figure 7:
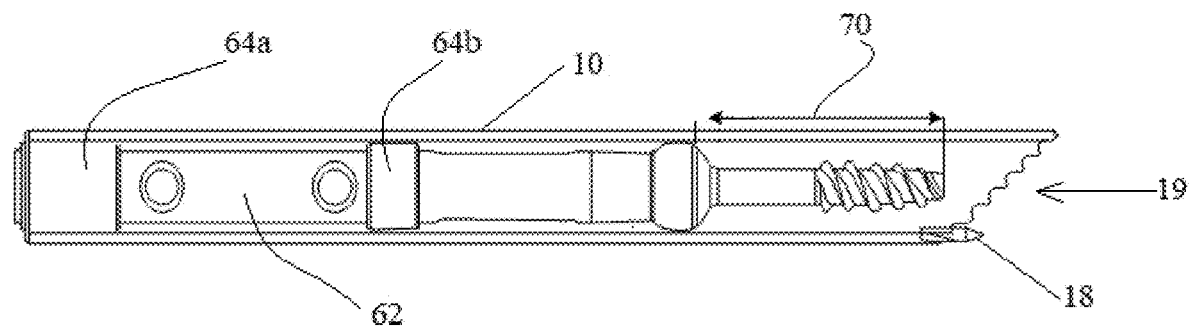
FIG. 7 depicts an example of the system wherein the drill (including a screw) is guided through a guide shaft.

FIG. 5 is a drawing of a drill used in the surgical system of the disclosure. The drill 50 includes a shaft 52 having one or more stabilization collars 54*a* and 54*b* that can be integral with the shaft or may be distinct in the form of bearing collars and the like. If one stabilization collar is present, the length of the collar is sufficient that the shaft remains substantially centered in the lumen 19 of the guide shaft 10 during use. The drill 50 includes a drill tip 56 at one end of the drill 50. The stabilization collars 54*a* and 54*b* have a diameter "D" which is slightly less (e.g., micrometers less) than the internal diameter of the guide shaft 10. The diameter of the stabilization collars 54*a* and 54*b* should be a diameter that allows the stabilization collars 54*a* and 54*b* to suitably slide into and out of the lumen 19 of the guide shaft 10 while reducing the lateral movement within the lumen 19, such that during operation of the drill the drill is held in a substantially steady position (see also FIG. 7).

Figure 6:
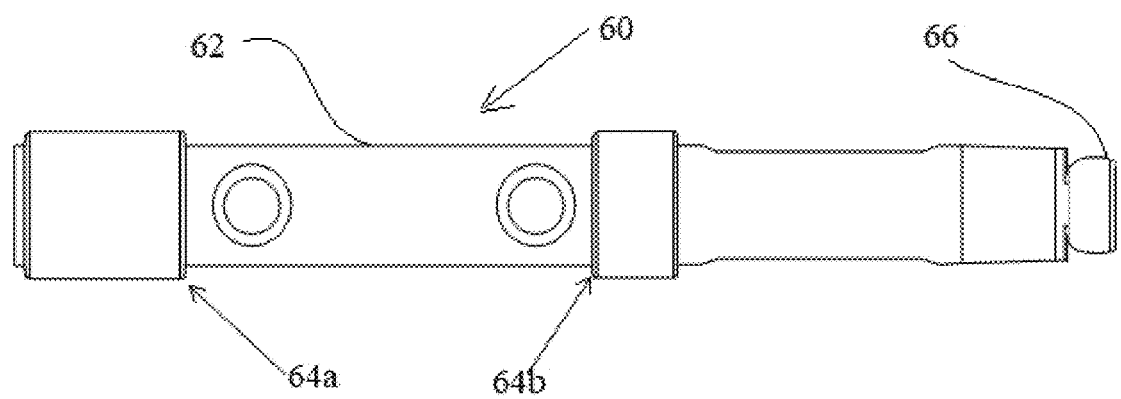
FIG. 6 provides a diagram of a screw-driver of the disclosure.

FIG. 6 depicts a screw-driver of the disclosure. Screw-driver 60 includes a shaft 62, a tip 66 for engaging a screw and stabilization collars 64*a* and 64*b*. The stabilization collars 64*a* and 64*b* have a diameter which is slightly less (e.g., micrometers less) than the internal diameter of the guide shaft 10. The diameter of the stabilization collars 64*a* and 64*b* should be a diameter that allows the stabilization collars 64*a* and 64*b* to slideably inserted into and out of the lumen 19 of the guide shaft 10 while reducing the lateral movement within the lumen 19, such that during operation of the screw-driver the screw-driver is held in a substantially steady position (see also FIG. 7, which depicts a screw 70 engaged with the screw-driver 60).

Figure 8A:
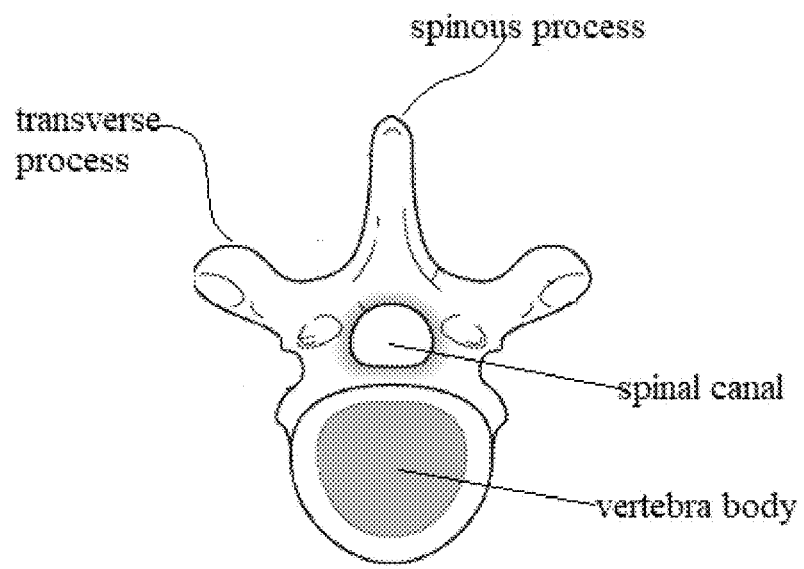
FIG. 8A is a general depiction of a spinal vertebrae.
Figure 8B:
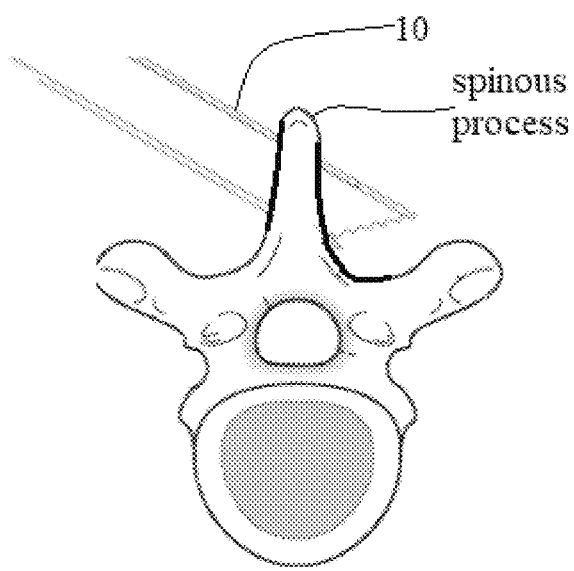
FIG. 8B depicts the process wherein the guide shaft is inserted through a hole in the spinal process cut by the hole cutter to reach the pedicle/transverse process opposite an incision site.

FIG. 8A depicts a general structure of a vertebrae, while FIG. 8B depicts the insertion of a guide shaft 10 of the disclosure through the spinous process.

Figure 9:
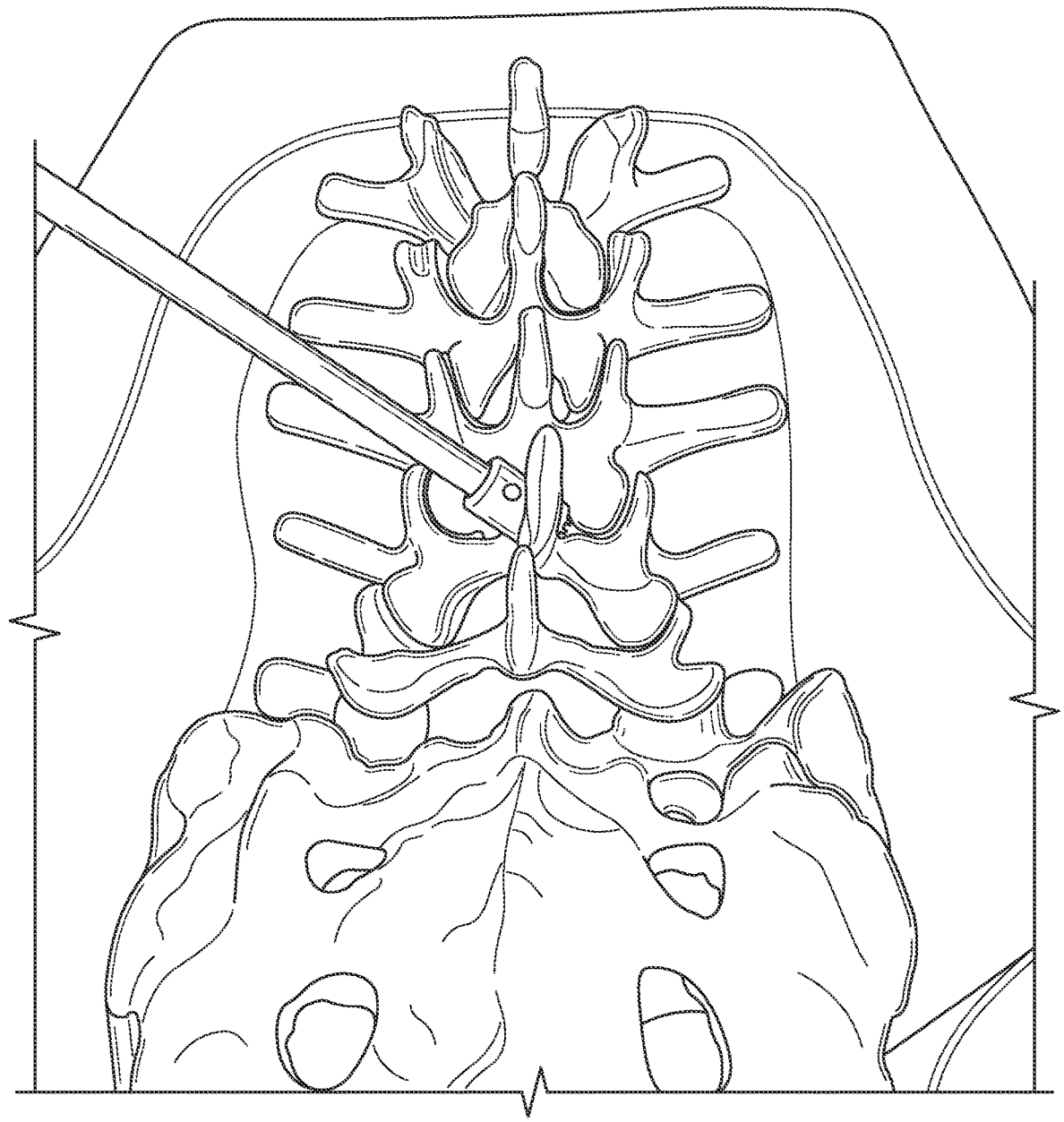
FIGS. 9 and 10 depict the use, surgical process using the devices of FIGS. 1-7 in the methods of the disclosure.

Turning to FIG. 9, the figure depicts the use of the hole cutter in boring a hole in the spinous process of a vertebrae. The hole cutter comprises a diameter that is smaller than the average diameter size of the average human spinous process. In addition, the hole cutter is equal to or slightly larger than the diameter of the external diameter of the guide shaft 10. The guide shaft 10 comprises an internal diameter equal to, or slightly larger (e.g., um to less than about 1 mm larger than the diameter of the drill and screw driver. Thus, once the guide shaft 10 is aligned then the drill and screw driver are aligned.

Figure 10:
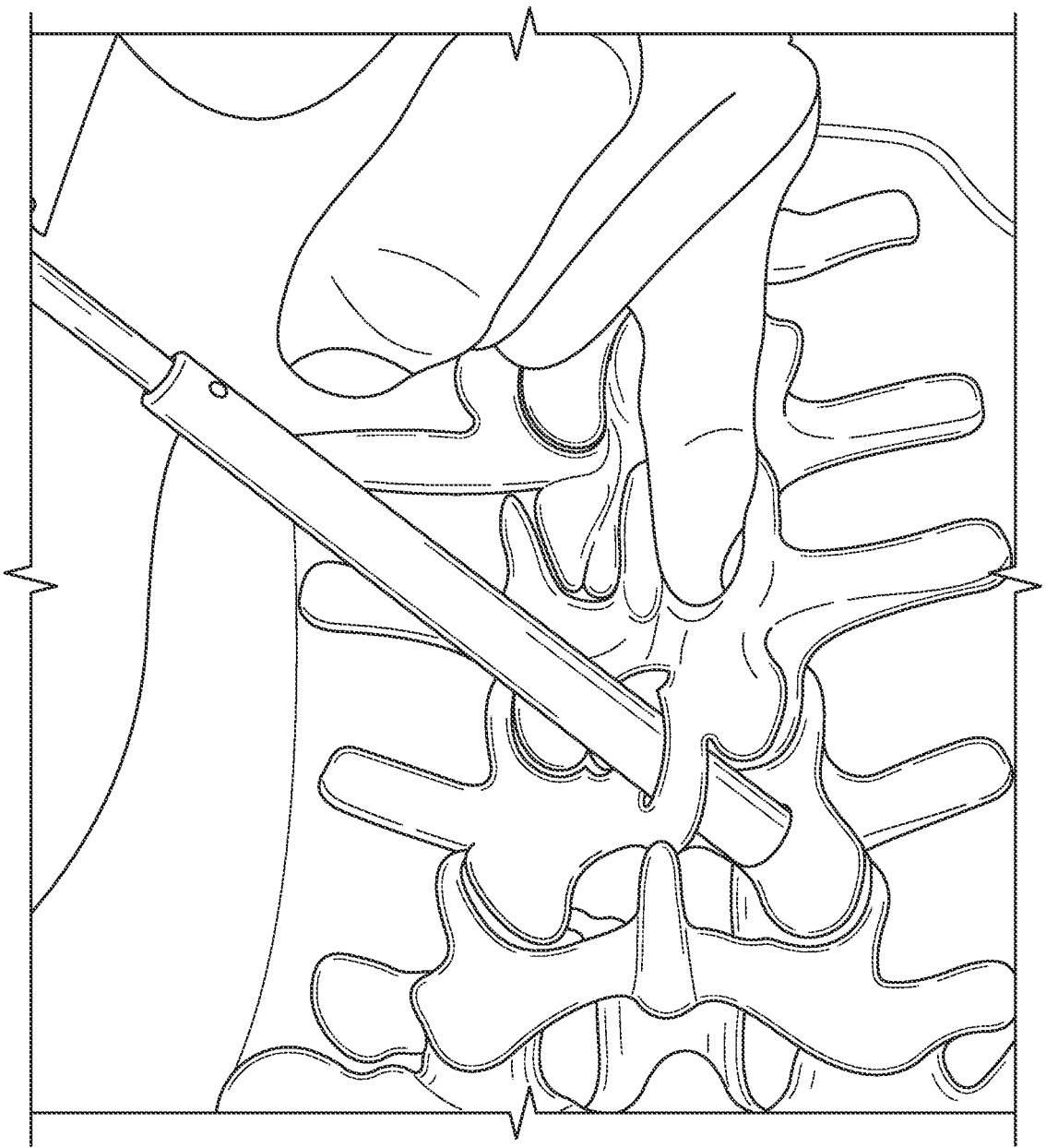

As shows in FIG. 9 an initial hole is made in the spinous process. The guide shaft 10 is inserted down to the facet joint (FIG. 10). Alignment can be confirmed with an oblique X-ray or through computer guidance.

The drill is then guided to the facet through the interior of the guide shaft 10. A drill hole is then made and a facet screw (e.g., FACET FIXX®, Nexxt Spine) is inserted using the screw driver 60. The screw driver 60 is detached from the screw 70. Pedicle screws are placed (e.g., with computer guidance or X-ray) and a rod and set screws are inserted.

In use the general process includes making a vertical line directly over the midline and a $2^{nd}$ vertical line over the pedicle using C-arm control. An incision is made over the marked area from pedicle to pedicle. The facet joint below and above is then exposed. A laminectomy is then carried out working toward the head to the level of the disc. The dura is retracted medially and a discectomy is carried out. The disc is prepared for fusion, bone graft is packed into the disc space followed by an appropriate-sized spacer.

On the incision side, pedicle screw placement is inserted using X-ray, K-wire and cannulated screw (this can be performed by a computerized guided system). A hole is made in the spinous process using the hole cutter 30. The guide shaft 10 is then inserted into the hole of the spinous process down to the facet joint. Computer guidance or oblique X-ray can be used to adjust and direct the guide shaft 10 accordingly. A drill hole is then made in the facet joint. The drill hole is aligned due to the inside diameter of the guide shaft 10. With the guide shaft 10 in place, a facet screw (e.g., FACET FIXX® TransLaminar Screw) is inserted and again there is alignment from the guide shaft 10. A mark on the screw driver will provide guidance as to when the screw is fully seated. The screwdriver 60 and guide shaft 10 are removed. The area is then decorticated and then packed with graft followed by the rod and set screws.

EXAMPLES

Study Design: A prospective study was carried out on fifty-nine informed participants. The study population included all patients with mild to moderate, central and peripheral stenosis. Pain intensity, was recorded using a visual analogue scale (VAS). The participants were in the 19 to 75 age range, the mean age was 58.7 years. The group consisted of 34 male and 25 female patients.

The follow up was performed for several months to years. The original series consisted of 62 patients but 3 were excluded due to lack of follow up. The information obtained in the study consisted of surgical time; hospitalization time; blood loss and documentation of union of the fusion site. All complications were documented including displacement of the spacer, wound healing or infection, and non-union.

The fusion was determined by X-Rays and CAT scan using Bridewell criteria. All cases had X-ray at 2 weeks, 3 months, 6 months, and 1 year post operation. Cases were considered a union if bone bridging across the disc was observed on X-ray or CT scan, there was no lucency around the fixation, there was no lucent line extending across the fusion mass. If there was a question of bone bridging on X-ray then a CAT scan was done. A total of 20 CAT scans were done.

The majority of the procedures were carried out at the L4-L5 (n=44) level and were single level procedures, however one two level procedure was carried out and a smaller number of procedures were carried out at different level beside L4-L5: L5-S1 (n=10), L3-L4 (n=2), L2-L3 (n=1).

There were four cases of documented non-union for a total percentage of 6.7% and they were all treated by anterior interbody fixation with healing. In one of these the spacer had migrated to the bone and was not able to be removed but did not appear to be a problem with the fusion.

During the TLIF procedure two types of spacers were used. There were 20 titanium spacers and 39 PEEK spacers. None of the titanium spacers displaced but they have a tendency to migrate and subside into the bone. This has also been noticed in other publications.

There was one case of deep infection, which occurred 3 months after the surgery. This patient has been admitted to a nursing home due to urinary tract infection, which seeded the surgical site. The infection completely resolved with a long term course of antibiotic while, treating the urinary infection. The bone disruption was not discovered until later date and it was treated by an anterior interbody fusion. At that time there was no evidence of acute infection but only extensive bone destruction. This went on to heal following the anterior interbody fusion.

The blood loss ranged from 30 cc to 250 cc and averaged 152.6 cc. Surgery time ranged from 1 hour 40 minutes to 3 hours 10 minutes, averaging 2 hours and 3 minutes.

It has been documented that MITLIF has many advantages ranging from less blood loss, less time in the hospital, to reduced post-operative pain. The technique that has just been described allows bilateral internal fixation through a single minimally invasive incision.

The fusion rate in a literature review of MITLIF by Goldstein revealed a fusion ranging from 0% to 16.7% averaging 3.2%. The non-union rate for this procedure is relatively high. A further research group had a non-union rate of 3.4%. This is attributed to improved technique as experience was obtained with this procedure.

There was no loosening of the facet screw unless there was also loosening of the pedicle screws and a non-union.

This procedure requires a moderate amount of muscle that needs to be removed. The removed muscle it is estimated to be in the order of three to four cubic centimeter. This is a relatively small amount of the cross section of the multifidus muscle. The facial attachments to the spinous processes remains intact. Furthermore this particular level is being fused. Clinically there does not appear to be any problem as result of removing this amount of muscle.

All cases were done with a computer guidance system (Brain Lab). This expedites the procedure and makes it easier. However the same procedure can be done using X-ray. A single oblique view is all that is necessary for placement of the facet screw. Once the screw is placed, anterior-posterior and lateral X-Ray can be made.

Because the facet screw is placed dorsal and distal to the nerve root there is minimal chance of nerve irritation during fixation. There was no clinical evidence of nerve root irritation in this series.

This series would tend to confirm that a unilateral decompression is adequate for moderate foramina and central stenosis. There are 2 factors that could have helped the decompression: (1) the side selected for decompression was the side with the most stenosis, and (2) in addition to the unilateral laminar and foramina direct decompression, the disc decompression would help both sides.

Since the exposure is medial to the facet joint, there is no exposure of the transverse processes for placement of graft. Some graft can be placed on the remaining superior facet joint below and the lower part of the superior facet joint above. Most of the fusion potential is from the intra discal graft.

What is claimed is:

1. A method of minimally invasive transforaminal lumbar interbody fusion (MITLIF) comprising:
    drilling a hole in a spinous process using a hole cutter;
    inserting a guide shaft into the hole of the spinous process down to a facet joint, wherein the guide shaft comprises a lumen defining an inner diameter of the guide shaft;
    inserting a drill through the lumen of the guide shaft, the drill having a shaft and at least one stabilization collar moving within the lumen of the guide shaft that maintains the shaft of the drill substantially centered in the lumen of the guide shaft;
    drilling a hole in the facet joint with the drill;
    inserting a facet screw and screwdriver though the inner diameter of the guide shaft; and
    inserting the facet screw into the facet joint with a screw-driver comprising at least one stabilization collars moving within the lumen of the guide shaft that maintains the shaft of the screw driver substantially centered in the lumen of the guide shaft.

2. The method of claim 1, further comprising placing pedicle screws on a side of the spinous process opposite to a side that the facet screw was placed.

3. The method of claim 2, wherein an access for placement of the pedicle and facet screws is the same access for both.

* * * * *